(12) United States Patent
O'Neil et al.

(10) Patent No.: US 7,113,815 B2
(45) Date of Patent: Sep. 26, 2006

(54) STACKED ADHESIVE OPTICAL SENSOR

(75) Inventors: Michael Patrick O'Neil, Sunnyvale, CA (US); Paul Mannheimer, Danville, CA (US); Rodney Chin, Oakland, CA (US); Adnan Merchant, Fremont, CA (US); Joseph Coakley, Dublin, CA (US); Don Hannula, San Luis Obispo, CA (US)

(73) Assignee: Nellcor Puritan Bennett Incorporated, Pleasanton, CA (US)

( * ) Notice: Subject to any disclaimer, the term of this patent is extended or adjusted under 35 U.S.C. 154(b) by 211 days.

(21) Appl. No.: 10/831,706

(22) Filed: Apr. 23, 2004

(65) Prior Publication Data

US 2004/0199063 A1    Oct. 7, 2004

Related U.S. Application Data

(63) Continuation of application No. 10/256,245, filed on Sep. 25, 2002, now Pat. No. 6,748,254.

(60) Provisional application No. 60/328,924, filed on Oct. 12, 2001.

(51) Int. Cl.
*A61B 5/00* (2006.01)

(52) U.S. Cl. .................... 600/344; 600/310; 600/323

(58) Field of Classification Search ............ 600/310, 600/322, 323, 344
See application file for complete search history.

(56) References Cited

U.S. PATENT DOCUMENTS

| 4,494,550 | A | | 1/1985 | Blazek et al. | |
|---|---|---|---|---|---|
| 5,584,296 | A | | 12/1996 | Cui et al. | |
| 5,638,593 | A | | 6/1997 | Gerhardt et al. | |
| 5,676,139 | A | | 10/1997 | Goldberger et al. | |
| 5,830,136 | A | | 11/1998 | Delonzor et al. | |
| 5,879,373 | A | * | 3/1999 | Roper et al. | 600/344 |
| 6,112,107 | A | | 8/2000 | Hannula | |
| 6,381,489 | B1 | * | 4/2002 | Ashibe | 600/344 |
| 6,415,167 | B1 | * | 7/2002 | Blank et al. | 600/344 |
| 6,839,583 | B1 | * | 1/2005 | Lewandowski et al. | 600/344 |
| 2003/0069484 | A1 | * | 4/2003 | Blank et al. | 600/310 |

* cited by examiner

*Primary Examiner*—Eric F. Winakur
(74) *Attorney, Agent, or Firm*—Fletcher Yoder

(57) ABSTRACT

An optical sensor having a cover layer, an emitter disposed on a first side of the cover, a detector disposed on the first side of said cover, and a plurality of stacked independent adhesive layers disposed on the same first side of the cover, wherein the top most exposed adhesive layer is attached to a patient's skin. Thus, when the sensor is removed to perform a site check of the tissue location, one of the adhesive layers may also be removed and discarded, exposing a fresh adhesive surface below for re-attachment to a patient's skin. The independent pieces of the adhesive layers can be serially used to extend the useful life of the product.

23 Claims, 4 Drawing Sheets

STACKED ADHESIVE OPTICAL SENSOR

CROSS-REFERENCE TO RELATED APPLICATION

The present application claims priority to U.S. Provisional Patent Application No. 60/328,924, filed Oct. 12, 2001, the teachings of which are incorporated herein by reference for all purposes.

BACKGROUND OF THE INVENTION

The present invention relates to optical sensors, and in particular to pulse oximeter sensors.

Many types of optical sensors are used to measure physiological characteristics of a patient. Typically, an optical sensor provides emitted light which is then scattered through a portion of a patient's tissue and detected. Various characteristics of a patient can be determined from analyzing such light, such as oxygen saturation, pulse rate, tissue bilirubin, etc.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

Certain types of optical sensors are applied to a patient's external tissue by way of an adhesive attachment, enabled by an adhesive layer on the sensor. During the monitoring of a patient, there is a need to remove the sensor to perform a site check of the tissue location, and this removal typically damages the adhesive layer. Furthermore, adhesive type sensors are often used with disposable type sensors where the photo emitter and the detector are mounted on a backing without the benefit of a rigid optical mount to maintain the emitter and detector's separation relatively fixed, and thus the sensor is subject to motion induced artifacts that may adversely affect measurement accuracy.

There is therefore a need to improve the functionality of adhesive-type optical sensors.

BRIEF SUMMARY OF THE INVENTION

The present invention provides an optical sensor having a cover layer, an emitter disposed on a first side of the cover, a detector disposed on the first side of said cover, and a plurality of stacked independent adhesive layers disposed on the same first side of the cover, wherein the top most exposed adhesive layer is attached to a patient's skin. Thus, when the sensor is removed to perform a site check of the tissue location, one of the adhesive layers may also be removed and discarded, exposing a fresh adhesive surface below for re-attachment to a patient's skin. The independent pieces of the adhesive layers can be serially used to extend the useful life of the product.

One aspect of the present invention is directed towards using a generally annulus-shaped adhesive layer that surround the emitter and the detector and thus avoids having any adhesive present between the emitter and the detector to minimize optical shunt, which is known to adversely affect measurement accuracy.

Another aspect of the present invention is directed towards using optical lenses made from a soft or compliant material such as an optically transparent PVC material to minimize tissue necrosis.

Another aspect of the invention is directed towards the use of a semi-rigid optical mount structure to hold the emitter and the detector in place to maintain the separation between the electro-optics (emitter and detector) relatively fixed and yet allow a certain minimal amount of torque and twisting to occur as the sensor is applied. The semi-rigid optical mount, by maintaining the separation relatively fixed reduces motion induced artifacts in the detected electro-optic signals, which may adversely interfere with measurement accuracy. For a further understanding of the nature and advantages of the present invention, reference should be made to the following description in conjunction with the accompanying drawings.

DETAILED DESCRIPTION OF THE INVENTION

Figure 1:
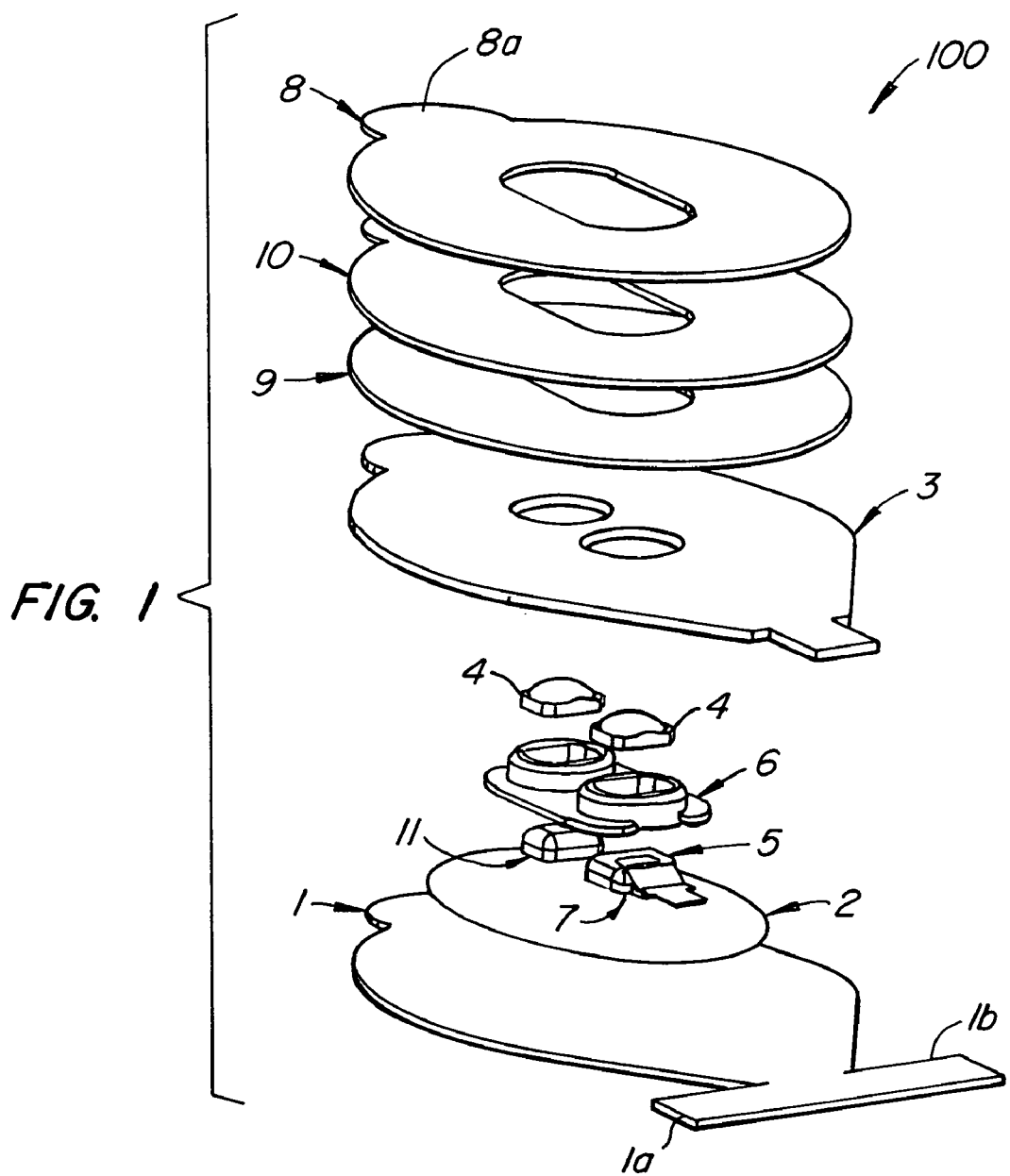
FIG. 1 is a perspective disassembled view of the sensor according to an embodiment of the present invention.

FIG. 1 is a perspective disassembled view of the sensor 100 according to an embodiment of the present invention. The sensor includes a sensor top 1 or cover layer which is exposed to the ambient environment when the sensor is attached to a patient's skin. In one embodiment, the cover layer 1 is fabricated of a common PVC foam. Alternately, the cover layer 1 is fabricated of a urethane foam material and particularly, an open cell breathable urethane foam such as, for example, the PORON™ family of urethanes commercially available from the Rogers corporation of Connecticut. A mask layer 2 preferably including a metalized plastic film is adhesively attached to the cover layer 1. In a preferred embodiment, the metalized masked layer 2 is an aluminized polypropylene film with a synthetic adhesive layer for attachment to the cover layer 1. The metalized mask layer 2 is so placed to prevent, minimize or reject secondary light from interfering with the photodetector 7. As used herein, secondary light includes all light that originates from sources other than the emitter 11, and which may have originated from sources including ambient or surgical light sources. An emitter 11 is placed above the mask layer 2. The emitter 11 is configured to direct light at predetermined wavelengths at a patient's skin. The light directed to the patient's skin is scattered through the patient's tissue and is selected to be of one or more wavelengths that are absorbed by the blood in an amount representative of the amount of blood constituent present in the body. A photo detector 7 is also placed above the mask layer 2 and adjacent to the emitter 11 to detect the amount of light that has been diffused through the patient's tissue. The amount of light that has diffused through the patient's tissue will vary in accordance with the changing amount of blood constituent in the tissue and the related light absorption.

For measuring blood oxygen level, the emitter is adapted to generate light of at least two different wavelengths, in accordance with known techniques for measuring blood oxygen saturation. The sensor, when adapted for blood oxygen saturation is useable for not only adult patients, but may also be adapted for use for neonatal and pediatric patients. Adaptations for neonatal and pediatric use may include accommodations of size and/or adhesive materials more compatible with the geometry and skin characteristics of those patients. Further, the sensor may optionally use emitters of different wavelengths and hence may use emitter and detector combinations that lead to more accurate readings at low blood oxygen saturations, which is the case for some patients. Light sources which are optimized for low oxygen saturation ranges are described in U.S. Pat. No. 5,782,237, entitled: "Pulse Oximeter and Sensor Optimized for Low Saturation," assigned to the assignee herein, the disclosure of which is hereby incorporated by reference herein in its entirety.

A Faraday shield 5 is placed in front of photodetector 7 to reduce the effect of extrinsic electrical fields that could adversely affect the electrical signal from the photodetector. A semi-rigid optical mount 6 is placed above the mask layer 2, and which surrounds and holds the emitter 11 and the detector 7 in a manner to maintain the separation between the emitter 11 and the detector 7 fixed and yet allow a certain minimal amount of flexing and twisting to occur as the sensor is applied to a patient. Without the semi-rigid optical mount in place, torque can often cause orientation changes between the emitter 11 and the detector 7 which can interfere with the accuracy of the measurements obtained by the sensor through changes in calibration and motion-induced artifact. Furthermore, the semi-rigid optical mount 6 substantially reduces the flex and the twist which may also create significant motion artifact, which is also known to adversely affect measurement accuracy. In one embodiment, the semi-rigid optical mount 6 is manufactured from a black polypropylene material. The black color of the optical mount also reduces the potential for optical shunt between the emitter and the detector, which can also cause measurement inaccuracies. Windows or lenses 4 are attached or bonded using a suitable adhesive (e.g., an ultraviolet cure adhesive process), one each to the detector and the emitter to assist in coupling the light emitted from the emitter 11 into the tissue, and collected from the tissue and directed towards the detector 7. In one embodiment, the lenses 4 are made of an optically transparent plastic material to minimize optical attenuation. In an alternate embodiment, the lenses 4 are made of a compliant material such as a transparent PVC, urethanes, or room temperature vulcanized (RTV) material, and so on. The choice of selecting a compliant material for the lenses is driven by the desire to prevent the possibility of necrosis of the skin, when the sensor is applied to the patient. Preferably, the compliant material has a hardness of less than 60 on a Shore A durometer scale. Alternately, or in addition to the lenses, the emitter and/or the detector arrangements may also include optical diffusers. The advantage of using optical diffusers is that the sensor would have less sensitivity to tissue heterogeneity, and thus provide more uniform and more accurate results.

A mask layer 3 is adhesively connected with the parts below it. The mask layer 3 has openings therein that fit over and surround the optical mount 6 placed below it (the mask layer 3). The mask layer 3 serves as a substantially flat platform for the subsequent attachment of the stack of adhesive layers. In one embodiment, the mask layer is fabricated from a cellular urethane foam such as the PORON™ family of urethane foams, and is attached to the cover layer 1 using a pressure sensitive adhesive. Lastly, a stack of adhesive layers 8, 9, and 10 are placed above the mask layer 3. The lower most adhesive layer 9 is attached to the mask layer 3 using an acrylic transfer adhesive. While in one embodiment a stack of three adhesive layers is placed above the mask layer 3, other multiple stacked adhesive layers are also within the scope of the embodiments of the present invention.

In one embodiment, the adhesive layers are in a ring shape so that no adhesive is present between the photo emitter 11 and the photo detector 7, thereby minimizing optical shunt between the photo emitter and the photo detector, which is known to lead to measurement inaccuracies. The adhesive layers or rings may be manufactured of a polyethylene film having an acrylic adhesive on one side for attachment to the patient's tissue. Alternately, the adhesive layers or rings may have an adhesive layers on both sides, in which case the adhesive layers are separated from one another by release layers (e.g. release paper). Preferably, the adhesive layers include a non-adhesive tab portion (e.g. 8a), arranged stacked or in a fanned-out array, to enable the clinician to easily grab and remove the used adhesive layer to expose the layer below. The tab portions may be non-adhesive colored tabs (e.g., green, yellow, red, lavender, orange) to enable the easy removal of the adhesive rings. Additionally, another release layer (not shown) is placed above the stack of adhesive layers to cover the very first adhesive layer while it is in storage.

In certain embodiments, the adhesive rings are black to minimize reflected light, which is known to impact the accuracy of optical-based measurements. In certain embodiments, the adhesive rings are thermally stable, so that the adhesion between the rings is not compromised as a result of exposure to heat. Additionally, the adhesive rings may include a release agent, such as, for example, a low molecular weight silicone oil on the back side of the ring, in order to minimize or prevent adjacent rings from sticking to one another. Various alternate ring construction may be employed, including a continuous 0.001 inch thick polyethylene film with acrylic pressure sensitive adhesive on one side. The continuous film can be made of other materials such as polyester, polyimide or Teflon, to achieve specific strength, release and temperature stability requirements. The adhesives used on the surface of the film can be acrylic, synthetic rubber, natural rubber (e.g., latex) or other non-toxic adhesive. The ring may include a paper with a release agent on one side as the carrier film. This allows printing on each release liner, user information such as "adhesive layer #1" or can be inked black to control optical shunt.

Alternately, the adhesive rings need not be in a ring shape, but may be continuous adhesive surface, with a black strip between the emitter and detector in order to minimize optical shunt.

The pre-attached stacks of adhesive layers enables the extended use of a disposable adhesive-type sensor. A desired feature for sensors is the ability to check the sensor site periodically (e.g. once every 12 hours), and remain capable of continuous use for multiple days. In prior disposable sensors which were adhesively attached to a patient's skin, multiple cycles of repositioning the sensor was not possible due to the degradation of the adhesive and the sloughing nature of the tissue beneath the sensor attachment location. This failed reattachment would necessitate the replacement of the sensor in its entirety, which would increase the overall cost of the patient monitoring procedure. However, with the use of a stack of pre-attached adhesive rings, when the sensor is removed to perform a site check, one of the adhesive layers may also be removed exposing a fresh adhesive surface below. Thus, having several independent pieces of adhesive layers that can be serially used, extends the useful life of the product and reduces the overall costs of the patient monitoring procedure.

Figure 2:
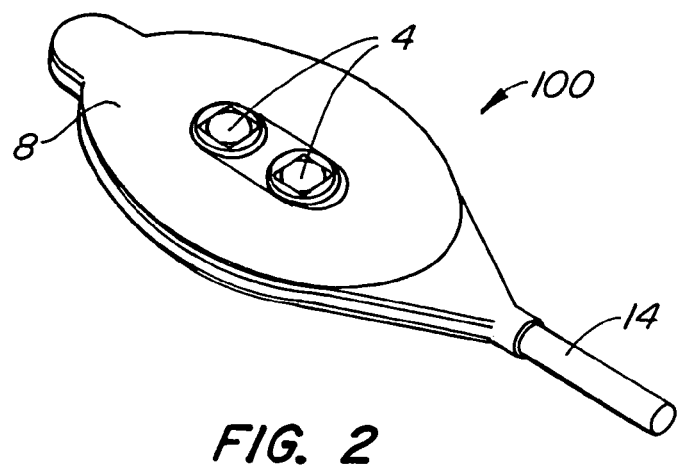
FIG. 2 is a perspective view of the sensor according to an embodiment of the present invention.

FIG. 2 is a perspective view of the assembled sensor 100. This figure (FIG. 2) shows the top most adhesive layer 8, and lenses 4 covering the photo emitter 11 and photo detector 7. Furthermore, FIG. 2 shows cable 14 attached to the sensor 100. Tab portions 1*a* and 1*b* (shown in FIG. 1) wrap around the cable 14 to hold the cable and the sensor in a stable manner. Cable 14 attaches to the photo emitter 11 and detector 7 via traces or wires (not shown).

Figure 3:
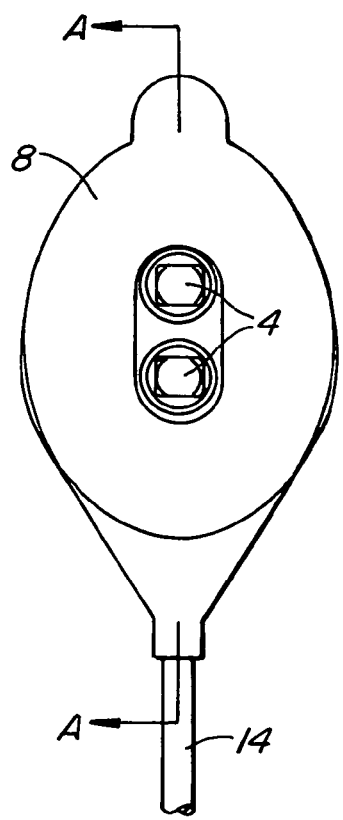
FIG. 3 is a top view of the embodiment of FIG. 2.
Figure 4:
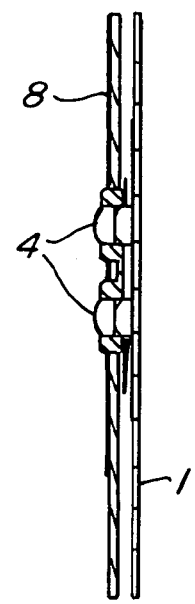
FIG. 4 is a sectional view "A—A" of FIG. 3.

FIG. 3 is a top view of the embodiment of FIG. 2. FIG. 3 also shows the top most adhesive layer 8, and lenses 4 covering the photo emitter 11 and photo detector 7. Furthermore, FIG. 2 shows cable 14 attached to the sensor 100. FIG. 4 shows sectional view "A–A" of FIG. 3. FIG. 4 shows the cover layer 1, the top most adhesive layer 8 and lenses 4 which are placed above the photo emitter 11 and photo detector 7. As can be seen from FIG. 4, the sensor 100 is substantially flat, while the lenses 4 protrude outward from a plane of the sensor. Thus, when attached, the lenses push on the patient's tissue location (e.g. forehead) to enhance light coupling and the depth of optical penetration by pressing mildly into the skin. Since the lenses protrude outward from the sensor plane, the adjacent adhesive layers necessarily lie in a plane which is offset or away from the patient's tissue location, thus "pulling" the lenses into the skin during use. This assures good optical contact between sensor and tissue, and reduces the potential contribution of light shunting.

Figure 5:
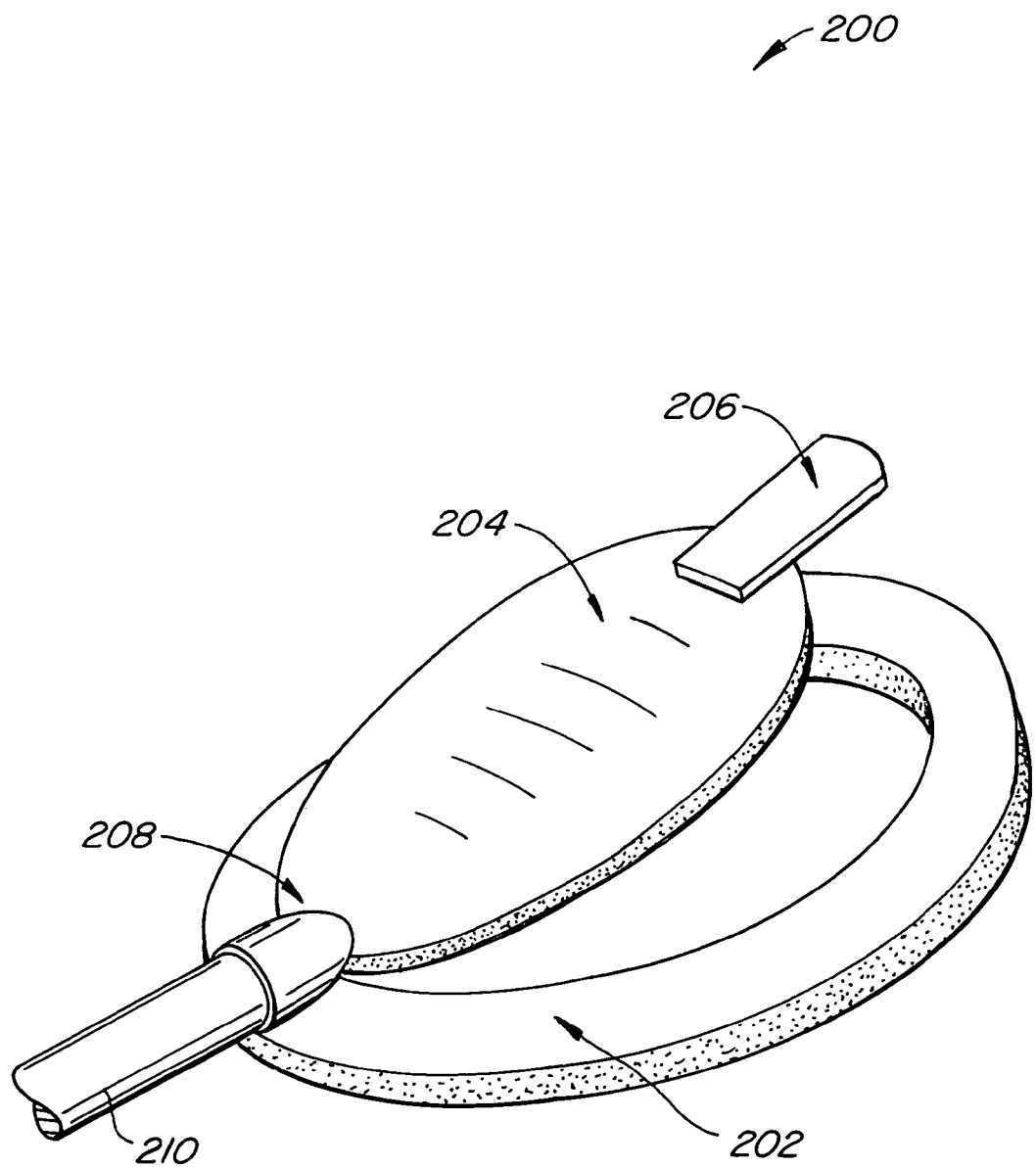
FIG. 5 is a perspective view of an alternate embodiment of the sensor of the present invention having a hinged lid.

FIG. 5 is a perspective view of an alternate embodiment of the sensor 200 of the present invention having a hinged lid. The sensor 200 includes a ring-shaped layer 202 having an adhesive side, which is configured to be attached to a patient during monitoring. The sensor 200 also includes a hinged lid 204 which holds the necessary electro-optics including a photo emitter and a photo detector (not shown) as described above. The hinged lid 204 is coupled to the ring-shaped adhesive layer 202 by a hinged connection 208 that enables the lifting and the checking of the sensor site without the need to remove the sensor from the patient. Cable 210 provides the leads or wires connected with the photo detector and photo emitter for the proper operation of the sensor. A clasp 206 secures the hinged lid 204 in a position effective for patient monitoring. The clasp 206 is also used by a clinician to lift the hinged lid 204 for checking the sensor site. In one embodiment, the clasp 206 adhesively engages the ring-shaped layer 202. In an alternate embodiment, the clasp 206 engages the ring-shaped layer via a mechanical clasp-type connection. The ring-shaped layer 202 may also incorporate a stacked adhesive arrangement as described above to enable the repeated removal and re-attachment of the sensor to the patient.

Figure 6:
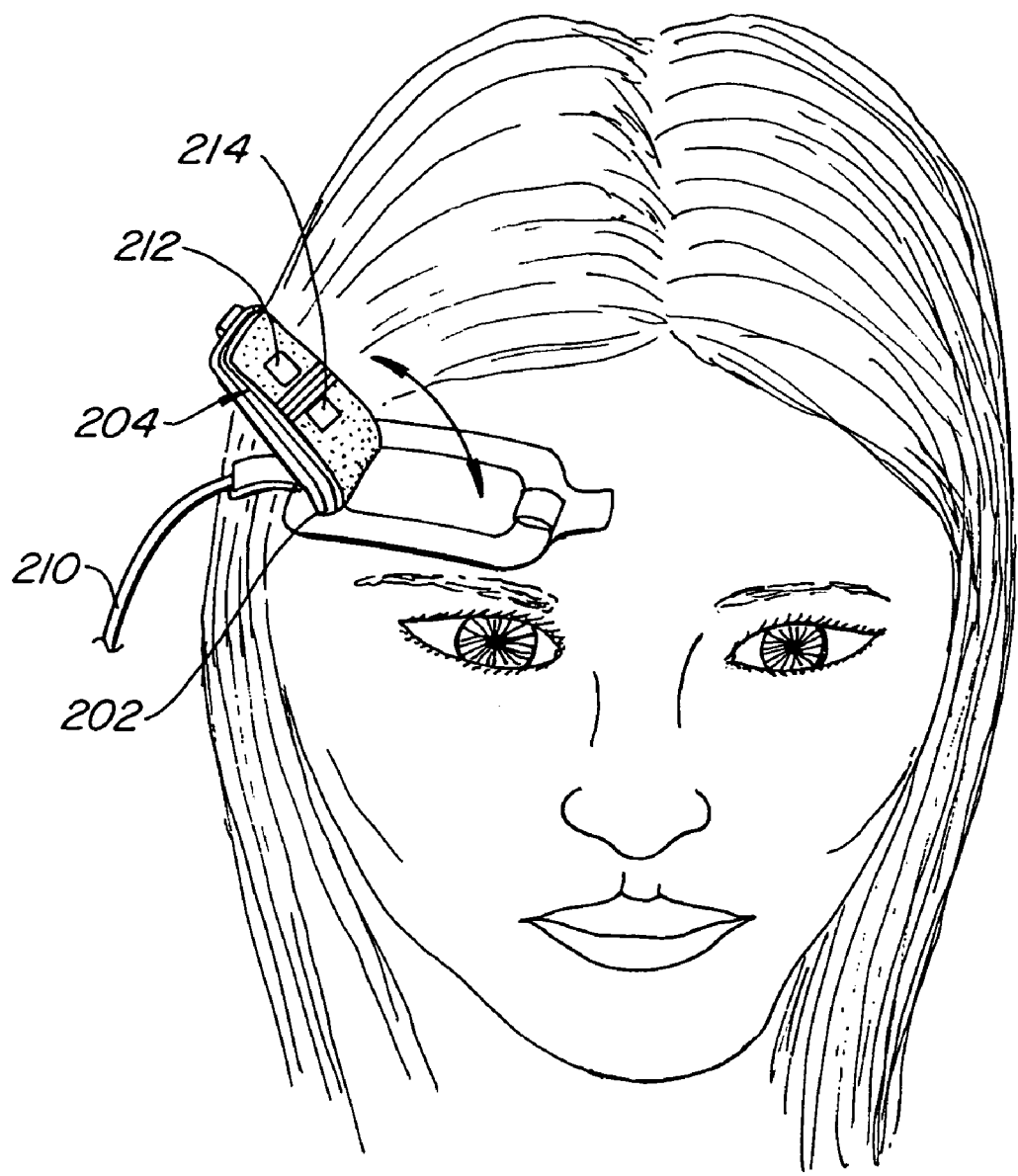
FIG. 6 is a diagram showing the sensor of FIG. 5 positioned on a patient during a site check.

FIG. 6 is a diagram showing the sensor of FIG. 5 positioned on a patient during a site check. As can be seen from this figure (FIG. 6), the ring-shaped layer 202 is adhesively attached to a patient, while the hinged lid 204 containing the photo emitter 212 and photo detector 214 is lifted from the patient's forehead to enable the checking of the tissue location underneath the sensor site. Cable 210 provides the leads or wires connected with the photo detector and photo emitter for the proper operation of the sensor.

The multiple stacked adhesive layer embodiments and the hinged lid embodiments of the present invention may be also be used to improve the operation of any disposable sensor and particularly disposable oximeter sensors. These disposable sensors include sensors based on the reflectance of light from tissue to the detector (as described above with the emitter and the detector placed on the same side of the tissue) as well as transmissive type sensors, where the emitter and the detector are placed on opposite sides of a tissue site being probed. Examples of sensors that can incorporate the multiple stacked adhesive layer embodiments or the hinged-lid embodiments include the adhesive, and reusable sensors for use at various tissue locations, including the finger tip, foot, nose, and forehead locations such as the D-20, D-25, N-25, I-20, R-15, as well as the A, N, I, and P series of sensors manufactured by the assignee herein.

Furthermore, the multiple stacked adhesive layer embodiments and the hinged lid embodiments of the present invention are not only useable for adult patients, but are also useable with patients on whom it is sometimes preferable to use a soft gel adhesive to minimize the occurrence of tearing of the skin. Such patients include geriatric, pediatric or neonatal patients. The inclusion of a soft gel in an optical sensor is described in U.S. Pat. No. 5,830,136, entitled: "Gel Pad Optical Sensor," assigned to the assignee herein, the disclosure of which is hereby incorporated herein in its entirety. An alternate embodiment of a soft gel adhesive includes only a single adhesive layer (not stacked), since some gel materials can be cleaned with water or other liquid agents to refresh the adhesive properties. As such, the use of multiple layers of gel adhesive may not be required for limited but multiple sensor placements on an individual patient.

As will be understood by those skilled in the art, the present invention may be embodied in other specific forms without departing from the essential characteristics thereof. For example, the disposable sensor may be a forehead or a nasal sensor, the sensor may be configured for use on an adult, pediatric or neonatal patient, the sensor may use several possible arrangements of adhesive layers arranged in an stacked manner, or the sensor may use suitable materials other than those described above. These other embodiments are intended to be included within the scope of the present invention, which is set forth in the following claims.

What is claimed is:

1. A sensor comprising:
   a generally annulus-shaped base, the base configured to attach to a tissue location on a patient;

a lid connected by a hinged connection at its near end with a near end of the base;

an emitter disposed on a first side of the lid;

a detector disposed on the first side of the lid; and a clasp connected with a far end of the lid and configured to engage a far end of the base.

2. The sensor of claim 1 comprising an adhesive layer disposed on a first side of the generally annulus-shaped base, the adhesive layer configured to adhere to a tissue location on a patient.

3. The sensor of claim 1 comprising a plurality of stacked independent adhesive layers disposed on a first side of the generally annulus-shaped base, the adhesive layers configured to adhere to a tissue location on a patient.

4. The sensor of claim 1 wherein the sensor is configured to operate in a first mode and a second mode, wherein in the first mode the clasp engages the base, and the lid and the base together form a substantially flat sensor, and wherein in the second mode, the clasp is disengaged from the base and the lid is lifted from the tissue location.

5. The sensor of claim 1 wherein the sensor comprises an oximeter sensor.

6. The sensor of claim 1 wherein the clasp engages the base via a mechanical clasp-type connection.

7. The sensor of claim 1 wherein the clasp adhesively engages the base.

8. A sensor comprising:

a base having an opening therein;

a lid sized to be disposed in the opening in the base, wherein one end of the lid is connected to the base by a pivotal connection;

a clasp connected with another end of the lid, the clasp configured to engage the base;

an emitter coupled to the lid; and a detector coupled to the lid.

9. The sensor of claim 8 comprising an adhesive layer disposed on a first side of the base, the adhesive layer configured to adhere to a tissue location on a patient.

10. The sensor of claim 8 comprising a plurality of stacked independent adhesive layers disposed on a first side of the base, the adhesive layers configured to adhere to a tissue location on a patient.

11. The sensor of claim 8 wherein the sensor is configured to have at least a first position and a second position, wherein in the first position the clasp engages the base, and the lid and the base together form a substantially flat sensor, and wherein in the second position, the clasp is disengaged from the base and the lid is pivotally lifted from a tissue location on a patient.

12. The sensor of claim 8 wherein the sensor comprises an oximeter sensor.

13. A sensor comprising:

a flexible base having an opening therein;

a flexible lid sized to be disposed in the opening in the base, wherein one end of the lid is connected to the base by a pivotal connection;

a clasp connected with another end of the clasp configured to engage the base;

an emitter coupled to the lid; and a detector coupled to the lid.

14. The sensor of claim 13 comprising an adhesive layer disposed on a first side of the base, the adhesive layer configured to adhere to a tissue location on a patient.

15. The sensor of claim 13 comprising a plurality of stacked independent adhesive layers disposed on a first tide of the base, the adhesive layers configured to adhere to a tissue location on a patient.

16. The sensor of claim 13 wherein the sensor is configured having at least a first position and a second position, wherein in the first position the clasp engages the base, and the lid and the base together form a substantially flat sensor, and wherein in the second position, the clasp is disengaged from the base and the lid is pivotally lifted from a tissue location on a patient.

17. The sensor of claim 13 wherein the sensor comprises an oximeter sensor.

18. A sensor comprising:

a base having an opening therein;

a lid sized to be disposed in the opening i the base, wherein one end of the lid is connected to the base by a pivotal conection;

a clasp connected with another end of the lid, the clasp configured to engage the base;

an emitter coupled to the lid;

a first lens coupled to the emitter;

a detector coupled to the lid; and a second lens coupled to the detector, wherein the first lens and the second lens protrude beyond a patient contact side of the base when the lid is disposed in the opening in the base.

19. The sensor of claim 18 wherein the first lens is coupled to the emitter and the second lens is coupled to the sensor using an adhesive.

20. The sensor of claim 18 comprising an adhesive layer disposed on a first side of the base, the adhesive layer configured to adhere to a tissue location on a patient.

21. The sensor of claim 18 comprising a plurality of stacked independent adhesive layers disposed on a first side of the base, the adhesive layers configured to adhere to a tissue location on a patient.

22. The sensor of claim 18 wherein the sensor is configured having at least a first position and a second position, wherein in the first position the clasp engages the base, and the lid and the base together form a substantially flat sensor, and wherein in the second position, the clasp is disengaged from the base and the lid is pivotally lifted from a tissue location on a patient.

23. The sensor of claim 18 wherein the sensor comprises an oximeter sensor.

* * * * *